United States Patent [19]

Garnham

[11] Patent Number: 5,776,715
[45] Date of Patent: Jul. 7, 1998

[54] BIOSENSORS FOR DETECTING NITRATE OR NITRITE IONS

[75] Inventor: Geoffrey William Garnham, Preston, United Kingdom

[73] Assignee: British Nuclear Fuels plc, United Kingdom

[21] Appl. No.: 586,901

[22] PCT Filed: May 30, 1995

[86] PCT No.: PCT/GB95/01235

§ 371 Date: Jan. 30, 1996

§ 102(e) Date: Jan. 30, 1996

[87] PCT Pub. No.: WO95/33068

PCT Pub. Date: Dec. 7, 1995

[30] Foreign Application Priority Data

May 28, 1994 [GB] United Kingdom ............. 9410805

[51] Int. Cl.⁶ ............ C12Q 1/66; C12Q 1/32; C12N 11/02; C12M 1/40
[52] U.S. Cl. ............ 435/8; 435/26; 435/176; 435/177; 435/287.1
[58] Field of Search ............ 435/174, 177, 435/175, 180, 8, 26, 287.1, 178, 176

[56] References Cited

U.S. PATENT DOCUMENTS

| 4,376,689 | 3/1983 | Nakamura et al. | 204/195 B |
| 4,791,055 | 12/1988 | Boguslaski et al. | 435/7 |
| 5,500,351 | 3/1996 | Eccles et al. | 435/25 |

OTHER PUBLICATIONS

Strehlitz, et al., Fresenius J. Anal. Chem. 349:676–678 (1994).

Kobayashi, et al., Agricultural & Biological Chemistry, vol. 45, Jun. 1981, pp. 1403–1408.

*Primary Examiner*—David M. Naff
*Attorney, Agent, or Firm*—Nixon & Vanderhye

[57] ABSTRACT

A biosensor for detecting nitrate or nitrite ions is provided containing a nitrate reductase or nitrite reductase for nitrate or nitrite ions, respectively, a co-factor such as NADPH, a photoluminescent ingredient and a transducer having a photodetector. The NADPH is oxidized to $NADP^+$ by reduction of nitrate or nitrite ions which directly or indirectly causes the photoluminescent ingredient to produce photons which are detected by the photodetector. The reductase and co-factor may be provided in an immobilized enzyme composition containing a co-enzyme such as alcohol dehydrogenase which produces the photons by inducing an oxidation reaction that converts $NADP^+$ back to NADPH to maintain a supply of NADPH to permit further reduction by the reductase. In the oxidation reaction, an alcohol such as hexanol or octanol is oxidized to its aldehyde with alcohol dehydrogenase from *Thermoanaerobium brockii*, and the aldehyde is detected by oxidizing $FMNH_2$ using luciferase. Nitrate reductase and nitrite reductase may both be present so that nitrite reductase can further reduce nitrite produced by nitrate reduction. The photons may be produced by one or more additional co-enzymes acting in a co-enzyme chain reaction.

13 Claims, 4 Drawing Sheets

BIOSENSORS FOR DETECTING NITRATE OR NITRITE IONS

BACKGROUND OF THE INVENTION

The present invention relates to biosensors and more particularly to biosensors for detecting nitrate or nitrite ions.

Owing to concern over the growing contamination of ground and surface waters by nitrates and nitrites both the field analysis and continuous monitoring of nitrate and nitrite concentrations are of significant interest. Conventionally, these species are detected in solution by wet chemical analysis methods which are time consuming and costly in terms of the personnel effort required.

An amperometric biosensor has in the prior art been proposed for nitrate detection based upon a reductase enzyme capable of accepting electrons from a mediating donor. However, the mediating donors proposed for use in such a biosensor, viz redox dyestuffs, produce a relatively negative redox potential (−400 mV to −700 mV) causing significant interference currents in real samples by the reduction of oxygen and other reducible substances present in the sample.

SUMMARY OF THE INVENTION

The purpose of the present invention is to provide an improved biosensor in which this problem is avoided.

According to a first aspect of the present invention, a biosensor comprises a biochemical capable of producing a biochemical reaction in the presence of nitrate or nitrite ions and a transducer arranged to detect a transducible output agent produced directly or indirectly by the reaction produced by the biochemical in the presence of nitrate or nitrite ions, the biochemical comprising a reductase for the nitrate or nitrite ions and a co-enzyme which is oxidised by reduction of the nitrate or nitrite ions and characterised in that the biochemical includes a photoluminescent ingredient which produces as the said output agent photons directly or indirectly by oxidation of the said co-enzyme and that the said transducer comprises a photodetector.

According to the present invention in a second aspect there is provided a biosensor for detecting nitrate or nitrite ions, the biosensor comprising an immobilised enzyme composition comprising a quantity of a nitrate or nitrite reductase enzyme, a quantity of a co-factor having a reduced state and an oxidised state and which is converted from its reduced state to its oxidised state by the reduction by the said reductase enzyme, a quantity of a co-enzyme capable of inducing an oxidation reaction in the presence of the co-factor in its oxidised state, the co-factor thereby being converted to its reduced state to maintain a supply of the co-factor in its reduced state to permit further reduction by the reductase enzyme, and means for detecting the extent of oxidation induced by the co-enzyme, the extent of oxidation by the co-enzyme being a measure of formation of the co-factor in its oxidised state which in turn is a measure of the quantity of nitrate or nitrite ions reduced by the reductase enzyme, the means for detecting comprising a photodetector for detecting photons emitted directly or indirectly as a result of oxidation induced by the co-enzyme.

The biosensor may include an immobilised enzyme composition which incorporates both a nitrate reductase and a nitrite reductase so that nitrite produced by the nitrate reduction is further reduced by the nitrite reductase.

According to the present invention in a third aspect there is provided a method of detecting nitrate and/or nitrite ions, the method comprising exposing to the nitrate or nitrite ions a biosensor as in the first or second aspect thereby causing the reductase enzyme to induce a reduction of the nitrate or nitrite ions and thereby produce by oxidation of the co-factor an output of photons, and detecting the output photons by the photodetector.

The co-factor may comprise the nicotinamide enzyme NADPH which is oxidised to $NADP^+$ in conjunction with the reduction provided by the reductase and subsequently re-reduced to NADPH by the oxidation by the co-enzyme thereby maintaining a supply of NADPH.

The co-enzyme may itself produce the photons or these may be produced via one or more other co-enzymes acting in a co-enzyme chemical chain.

The said photons may be produced by the enzyme luciferase. This may be employed in a biochemical chain reaction together with NADPH for example in the manner described below.

The reductases may conveniently be employed together with the nicotinamide co-factor NADPH as a co-factor which is oxidised to $NADP^+$ by the reduction of $NO_3^-$ or $NO_2^-$ ions by the reductases. The production of $NADP^+$ may be detected by oxidation of a further reductant, the oxidation thereby producing directly, or by inducing of further oxidation-reduction reactions, the output photons.

For example, the production of $NADP^+$ may be detected by the oxidation of an alcohol, eg a primary or secondary alcohol, eg an aliphatic alcohol such as hexanol or octanol, to its corresponding aldehyde, eg in the presence of an alcohol dehydrogenase, eg TADH which is obtained from *Thermoanaerobium brockii*. The aldehyde so produced may be detected by reaction with reduced flavin $FMNH_2$ in the presence of oxygen together with the enzyme luciferase to catalyse the reaction. Luciferase may be obtained from *Vibrio harveyi*, and is commercially available. It is very sensitive to the presence of aldehyde and can detect concentrations as low as pmol quantities providing light emission from the reaction it catalyses. The intensity of emitted light provides a measure of the $NADP^+$ converted to NADPH which in turn provides a measure of nitrate or nitrite concentration present. Examples of such reaction chains are illustrated below.

Suitable reductase enzymes are commercially available or may be isolated in a known way from fungi, micro-algae or plants. For example, for nitrate reduction this enzyme may comprise Aspergillus species (EC 1.6.6.2). For nitrite reduction these enzymes may for example comprise *Escherichia Coli* (EC 1.9.6.1) which may be readily isolated in a known way from aerobic bacteria or algae and higher plants. Such enzymes may, as is known in the prior art, require the presence of a known activator, eg FAD.

Such reductase enzymes may be stabilised in a manner known to those skilled in the art, eg as described in EP 244,771.

In the biosensor according to the present invention it is desirable to immobilise and stabilise the biochemical agent (s) in close proximity to the transducer so that the enzymes remain active for long periods (eg months or years) and are not lost from the sensor. As in the prior art, immobilisation may be achieved by adsorption on an organic or inorganic carrier, physical inclusion in a gel, behind a semi-permeable membrane, cross-linking by bifunctional or multifunctional reagents or covalent bonding to the transducer either directly or using a linker.

The biosensor according to the present invention provides a convenient means for measuring the concentration of nitrate and/or nitrite ions in a given sample. As the biosensor is not amperometric it does not suffer from the problem of interference currents experienced with the amperometric biosensors of the prior art and therefore can be designed to be inherently more accurate. Bioluminescent biosensors offer the further advantages of high specificity and high sensitivity to the ions to be detected. Furthermore, the biosensor according to the present invention has the advantage that the co-factor, eg NADPH, oxidised in conjunction with the reductase action, is in an oxidation-reduction cycle and therefore a constant supply of the co-factor is maintained without need for replenishment.

BRIEF DESCRIPTION OF THE DRAWINGS

Embodiments of the present invention will be described by way of example with reference to the accompanying drawings, in which.

DETAILED DESCRIPTION OF THE INVENTION

Figure 1:
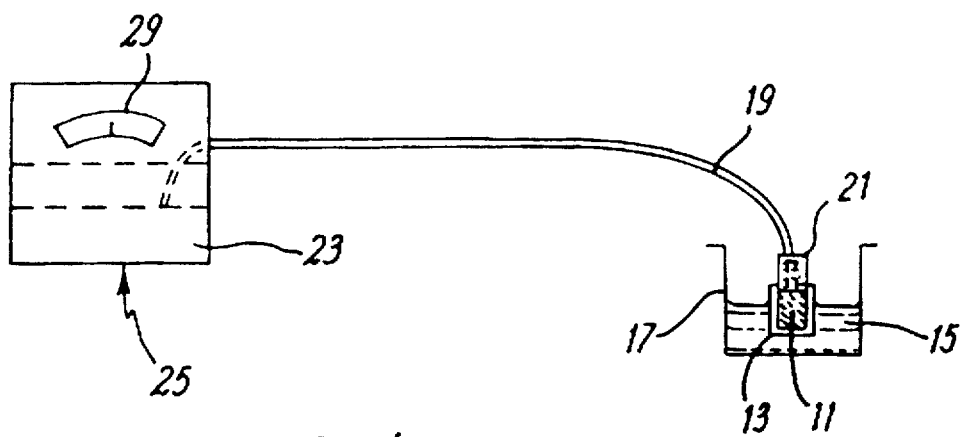
FIG. 1 is a side view of a biosensor arrangement embodying the present invention.

As shown in FIG. 1, a biosensor arrangement comprises an immobilised and stabilised enzyme layer 11 incorporating a reductase which is coated with a semi-permeable membrane 13 in a sample 15 of an aqueous solution to be investigated, held in a vessel 17. A fibre-optic cable 19 is fitted via a ferrule 21 to make contact at one of its ends with the layer 11. The other end of the cable 19 is connected to a photodetector 23 incorporated within a luminometer 25. Outputs from the photodetector 23 are processed by an electronics unit 27 within the luminometer 25 and output signals are visually indicated on a display 29.

In use of the arrangement shown in FIG. 1, nitrate or nitrite ions to be detected in the sample 15 are reduced in one of the ways described herein by the enzymes in the layer 11 and photons are produced by an appropriate series of chemical reactions, the number of photons being a measure of the concentration of the nitrate or nitrite ions reduced and therefore present. The photons are detected by the photodetector 23 via the cable 19 and the output of the photodetector is employed to operate the display 29 to give an indication of the level of the concentration of nitrate or nitrite ions detected.

Figure 2:
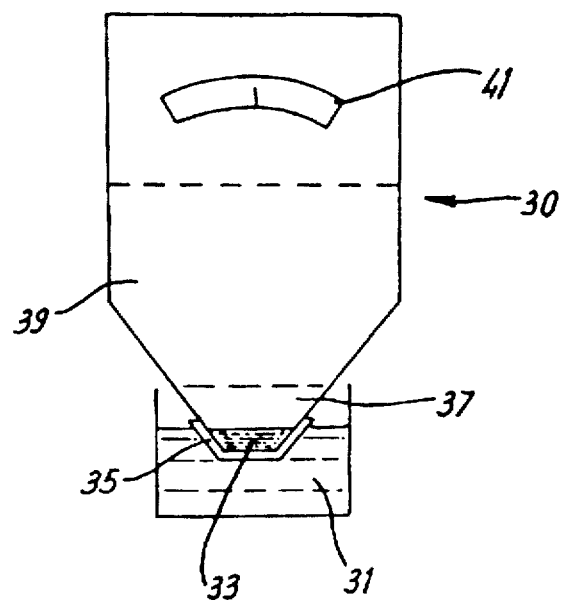
FIG. 2 is a side view of an alternative biosensor arrangement embodying the present invention.

The arrangement shown in FIG. 2 is similar to that shown in FIG. 1 except that the immobilised enzyme layer forms part of the luminometer indicated in FIG. 1 by numeral 30 and so no fibre-optic cable is required between the two. Thus, in FIG. 2, nitrate/nitrite ions in a sample 31 are converted by a stabilised and immobilised enzyme layer 33 with which they make contact via a semi-permeable membrane 35 and resulting photons generated in the layer 33 are detected directly by a photodetector 37 adjacent to the layer 33 which via an electronics unit 39 provides an output signal for indication on a display 41.

Figure 3:
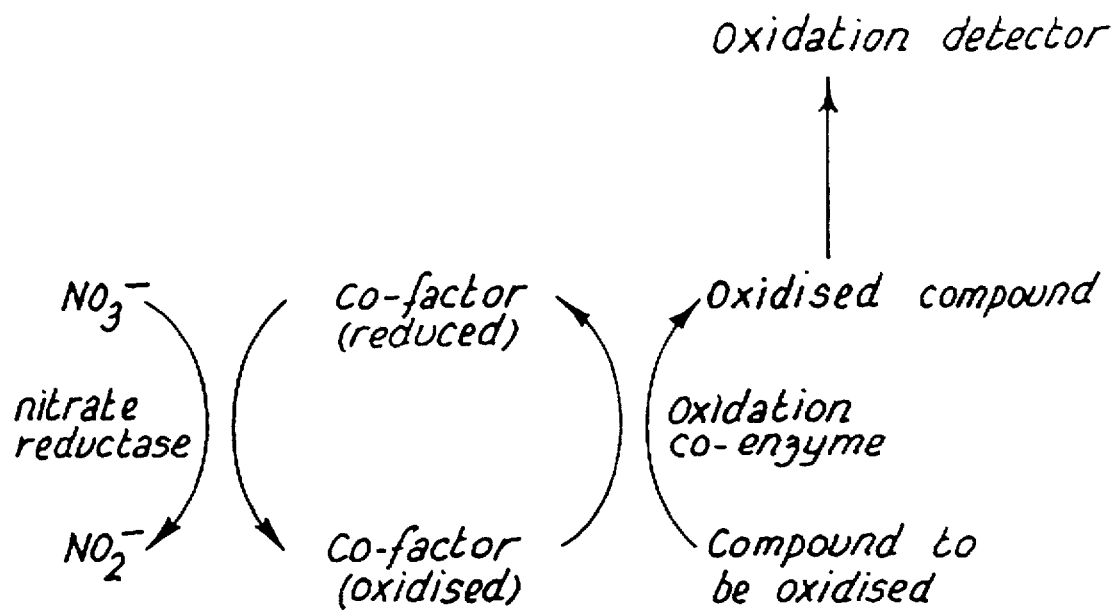
FIG. 3 is a diagrammatic representation of a generalised process involving biochemical reactions which may be employed in biosensors embodying the present invention.

FIG. 3 illustrates a general reaction scheme illustrating operation of a biosensor embodying to the present invention. Nitrate ions to be detected are reduced by a nitrate reductase to nitrite with concomitant oxidation of a co-factor to its oxidised state, eg from NADPH to $NADP^+$. The amount of co-factor in the oxidised state is detected by re-reduction of the co-factor to its reduced state, thereby maintaining a supply of the co-factor in that state, by the action of an oxidation co-enzyme which concomitantly brings about oxidation of a compound to be oxidised to an oxidised compound, the amount of the oxidised compound produced being detected directly or indirectly by an bioluminescent oxidation detector in one of the ways described above with reference to FIG. 1 or 2. For example, the compound to be oxidised may be an alcohol, the oxidation co-enzyme may be an alcohol dehydrogenase and the oxidised compound may be an aldehyde.

Figure 4:
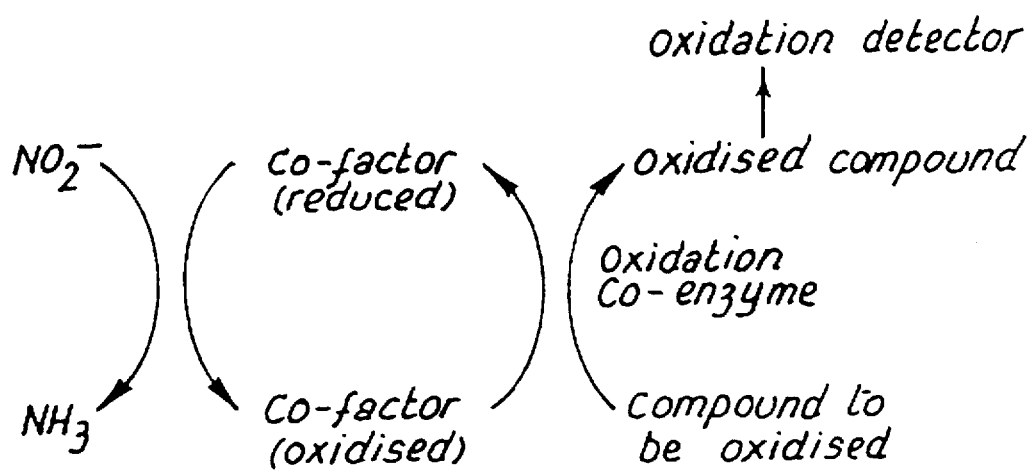
FIG. 4 is a diagrammatic representation of a generalised process involving biochemical reactions which may be employed in biosensors embodying the present invention.

FIG. 4 illustrates a general reaction scheme illustrating operation of a biosensor for nitrite detection. The nitrite ions might be produced following reduction of nitrate ions in the matter illustrated in FIG. 3. Alternatively, the nitrite ions might exist already. The reactions illustrated in FIG. 4 operate in a similar manner to those illustrated in FIG. 3 except that nitrite is reduced by nitrite reductase to $NH_3$ in FIG. 4.

Examples of immobilised enzyme layers for use in the above embodiments will now be described. In the following examples it is assumed that nitrate or nitrite ions exist in the measured sample.

EXAMPLE 1

Luciferase bioluminescent coupled system for nitrate reduction

Figure 5:
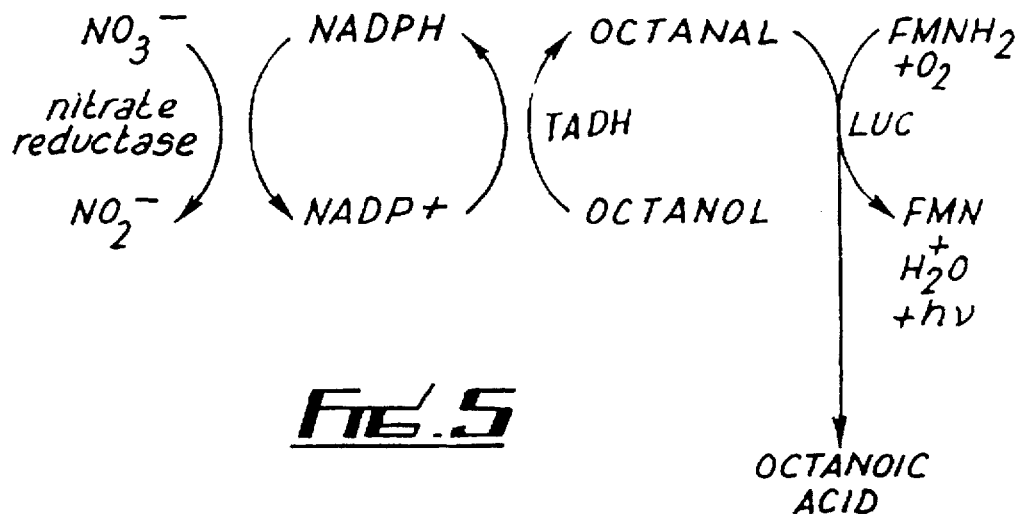
FIG. 5 is a diagrammatic representation of an example of a biochemical process which may be employed in biosensors embodying the present invention.

This example is illustrated in FIG. 5. In this case the reductase converts $NO_3^-$ to $NO_2^-$ and NADPH is oxidised to $NADP^+$. This oxidised product is re-reduced by the oxidation of octanol to octanal brought about by the co-enzyme alcohol dehydrogenase which may be obtained from the commercially available *Thermoanaerobium brockii*. The alcohol dehydrogenase is represented in FIG. 5 by TADH. The octanal is reacted with reduced flavin, $FMNH_2$ in the presence of oxygen and catalysed by luciferase, LUC and the products octanoic acid, FMN oxidoreductase and water are produced as illustrated in FIG. 5 and light is caused to be generated and this may be detected in the manner described with reference to FIG. 1 or FIG. 2.

As noted above, bioluminescent biosensors promise high specificity due to the enzymic reaction and a sensitivity sufficient to register quanta of light. Luciferase is preferably the enzyme responsible for the light-emitting reaction of luminous bacteria and may be employed as illustrated in FIG. 5 to catalyse the reaction of molecular oxygen with reduced flavin and aliphatic aldehyde to form long-lived intermediates whose breakdown provides energy to give light emission with reasonably high quantum yield (~10%)⁻, as follows:

$$FMNH_2 + RCHO + O_2 \rightarrow FMN + RCOOH + H_2O + h\nu$$

RCHO represents the aliphatic aldehyde and hv represents light.

The reduced flavin may be generated in situ by specific NAD(P)H: FMN oxidoreductases $$NAD(P)H + FMN + H^+ \rightarrow NAD(P)^+ FMNH_2$$

and thereby coupled in with the target system via the NADP$^+$ dependent alcohol dehydrogenase.

EXAMPLE 2

Luciferase bioluminescent coupled system for nitrite reduction

Figure 6:
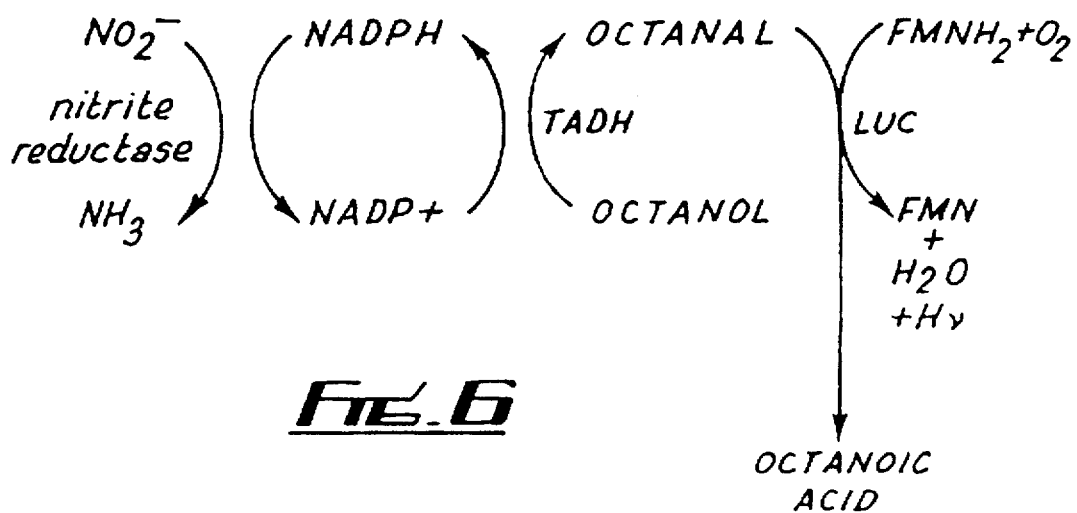
FIG. 6 is a diagrammatic representation of another example of a biochemical process which may be employed in biosensors embodying the present invention.

This example is illustrated in FIG. 6. The process is carried out in a manner similar to that for nitrate detection as shown in FIG. 5 except that nitrite reductase is used instead of nitrate reductase, and ammonia is produced by reduction of the nitrite.

The output light produced by the method illustrated in FIG. 6 is detected in the manner illustrated in FIG. 1 or FIG. 2.

EXAMPLE 3

Alternative system for nitrate reduction

Figure 7:
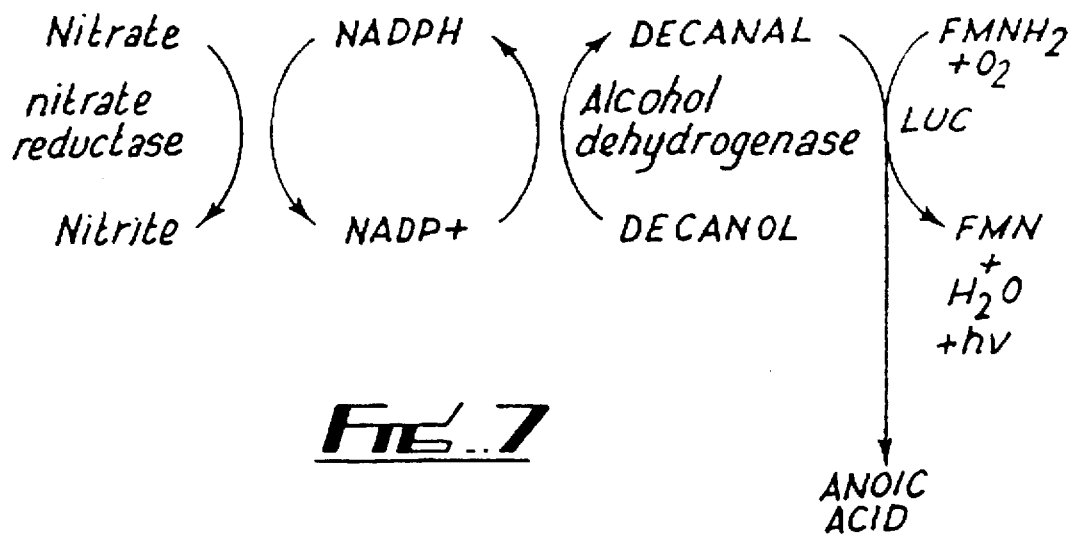
FIG. 7 is a diagrammatic representation of an example of a biochemical process which may be employed in biosensors embodying the present invention.

This example is illustrated in FIG. 7. It is an alternative to that shown in FIG. 5. The process is carried out in a manner similar to that shown in FIG. 5 except that the oxidation of octanol to octanal by TADH is replaced by a similar oxidation of decanol to decanal which is subsequently oxidised to decanoic acid.

EXAMPLE 4

Figure 8:
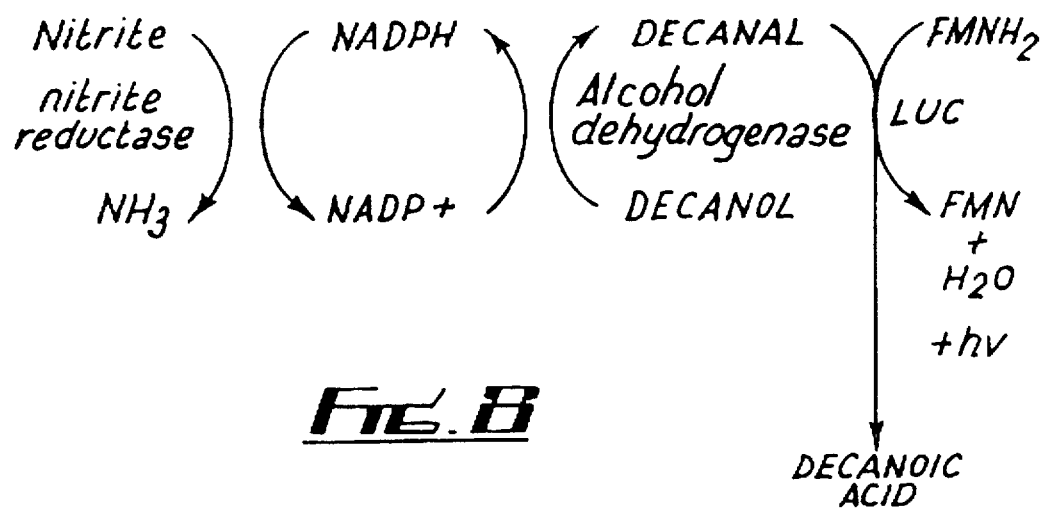
FIG. 8 is a diagrammatic representation of an example of a biochemical process which may be employed in biosensors embodying the present invention.

This example is illustrated in FIG. 8. It is an alternative to that shown in FIG. 6. The process is carried out in a manner similar to that illustrated in FIG. 7 except that the initial reduction step is nitrite to NH$_3$ by nitrite reductase.

In examples 3 and 4 the decanol may be Z-tetradecanol and the decanal may be Z-tetradecanal. The alcohol dehydrogenase co-enzyme may be *Thermoanaerobium ethanolicus* alcohol dehydrogenase.

In Examples 1 to 4 the FMN produced may be re-reduced to FMNH$_2$ by a NADH-specific FMN oxido-reductase thereby maintaining a supply of FMNH$_2$.

I claim:

1. A biosensor for detecting nitrate or nitrite ions which comprises a reductase, a co-factor, a photoluminescent ingredient and a transducer, said transducer comprising a photodetector, said reductase being a reductase for nitrate or nitrite ions, said co-factor being oxidized by the reduction of the nitrate or nitrite ions, oxidation of said co-factor directly or indirectly causing said photoluminescent ingredient to output photons, said output photons being detected by said photodetector.

2. The biosensor as claimed in claim 1 wherein said reductase and said co-factor are provided in an immobilized enzyme composition, said immobilized enzyme composition comprising a co-enzyme, said co-enzyme being capable of inducing an oxidation reaction in the presence of said co-factor in its oxidized state, said co-factor thereby being converted back to its reduced state to maintain a supply of said co-factor in its reduced state to permit further reduction by said reductase, said co-enzyme directly or indirectly causing said photoluminescent ingredient to output said output photons, said output photons being a measure of the extent of the oxidation induced by said co-enzyme, the extent of oxidation by said co-enzyme being a measure of the formation of the co-factor in its oxidized state, the measure of the co-factor in its oxidized state in turn being a measure of the quantity of nitrate or nitrite ions reduced by the reductase.

3. The biosensor as in claim 2 wherein said immobilized enzyme composition incorporates both a nitrate reductase and a nitrite reductase so that nitrite produced by the nitrate reduction is further reduced by the nitrite reductase.

4. The biosensor as in claim 1 wherein the said co-factor that is oxidized comprises NADPH which is oxidized to NADP$^+$ in conjunction with the reduction provided by the reductase.

5. The biosensor as in claim 1 wherein said output photons are produced via one or more co-enzymes in combination with said co-factor acting in a co-enzyme chain reaction.

6. The biosensor as in claim 1 wherein said output photons are produced by luciferase in a biochemical chain reaction together with NADPH.

7. The biosensor as in claim 4 further comprising an organic alcohol and alcohol dehydrogenase, wherein oxidation of NADP$^+$ is detected by oxidation of said organic alcohol, by said alcohol dehydrogenase, to its corresponding aldehyde.

8. The biosensor as in claim 7 wherein the aldehyde is detected by reaction with FMNH$_2$ in the presence of oxygen together with luciferase to catalyze the reaction.

9. A biosensor for detecting nitrate or nitrite ions which comprises a reductase, a co-factor, a co-enzyme, a photoluminescent ingredient and a transducer, said transducer comprising a photodetector, said reductase being a reductase for nitrate or nitrite ions, said co-factor comprising NADPH, said NADPH being oxidized to NADP$^+$ by the reduction of the nitrate or nitrite ions, said NADP$^+$ being reduced to NADPH upon oxidation induced by of said co-enzyme, oxidation by said co-enzyme directly or indirectly causing said photoluminescent ingredient to output photons, said output photons being detected by said photodetector.

10. The biosensor according to claim 9 further comprising alcohol dehydrogenase and an organic alcohol selected from the group consisting of hexanol, decanol, octanol and mixtures thereof, wherein oxidation of NADP$^+$ is detected by oxidation of said organic alcohol, by said alcohol dehydrogenase, to its corresponding aldehyde.

11. The biosensor according to claim 10 wherein said aldehyde is detected by reaction with FMNH$_2$ in the presence of oxygen and with luciferase as said photoluminescent ingredient.

12. The biosensor according to claim 9 wherein said co-enzyme is of alcohol dehydrogenase obtained from *Thermoanaerobium ethanolicus*.

13. A biosensor for detecting nitrate or nitrite ions which comprises a reductase, a co-factor, a co-enzyme, a photoluminescent ingredient and a transducer, said transducer comprising a photodetector, said reductase being a reductase for nitrate or nitrite ions, said co-factor comprising NADPH, said co-enzyme oxidizing decanol or tetra-Z-decanol, said photoluminescent ingredient being luciferase, said NADPH being oxidized to NADP$^+$ by the reduction of the nitrate or nitrite ions, said NADP$^+$ being reduced to NADPH upon oxidation of decanol or tetra-Z-decanol to decanal or tetra-Z-decanal respectively in the presence of alcohol dehydrogenase obtained from *Thermoanaerobium ethanolicus*, oxidation of said decanol or tetra-Z-decanol being detected by reaction of decanol or tetra-Z-decanol with FMNH$_2$ in the presence of oxygen and said luciferase, said luciferase outputting output photons, said output photons being detected by said photodetector.

* * * * *